United States Patent [19]

Grollier et al.

[11] Patent Number: 4,832,943
[45] Date of Patent: May 23, 1989

[54] COMPOSITION FOR COLORING SKIN

[75] Inventors: Jean F. Grollier, Paris; Georges Rosenbaum, Asnieres, both of France

[73] Assignee: L'Oreal, Paris, France

[21] Appl. No.: 939,813

[22] Filed: Dec. 9, 1986

[30] Foreign Application Priority Data

Dec. 11, 1985 [LU] Luxembourg .................... 86202

[51] Int. Cl.$^4$ ..................... A61K 7/021; A61K 7/40
[52] U.S. Cl. ..................... 424/59; 424/60; 424/63; 514/937; 514/944
[58] Field of Search ..................... 424/59, 60, 63

[56] References Cited

U.S. PATENT DOCUMENTS

| | | | |
|---|---|---|---|
| 3,272,713 | 9/1966 | Runge | 424/59 |
| 3,920,808 | 11/1975 | Fusaro | 424/59 |
| 4,118,423 | 10/1978 | Vanlerberghe et al. | 424/59 |
| 4,228,151 | 10/1980 | Lang et al. | 424/59 |
| 4,293,542 | 10/1981 | Lang et al. | 424/60 |
| 4,293,543 | 10/1981 | Cotte et al. | 424/59 |
| 4,434,154 | 2/1984 | McShane | 424/60 |
| 4,609,544 | 9/1986 | Herlihy | 424/60 |

FOREIGN PATENT DOCUMENTS

| | | | |
|---|---|---|---|
| 2051947 | 9/1970 | Fed. Rep. of Germany | 424/59 |
| 2466492 | 4/1981 | France | 424/59 |

OTHER PUBLICATIONS

Seifen-Öle-Fette-Wachse, vol. 99, No. 10, May 1973, pp. 263–264.
Fette-Seifen-Anstrichmittel, vol. 69, No. 6, 1967, p. 420.

Primary Examiner—Dale R. Ore
Attorney, Agent, or Firm—Cushman, Darby & Cushman

[57] ABSTRACT

A two-component pack containing a composition for coloring or artifically tanning skin comprising two components (a) and (b) intended to be mixed at the time of use or to be applied to the skin successively wherein component (a) comprises meso-tartaraldehyde in the form of an aqueous solution, an aqueous gel or an aqueous emulsion, and component (b) comprises at least one hydroxyquinone, which is 2,5-dihydroxy-3-methyl-1,4-benzoquinone, 2,5-dihydroxy-3-methyl-6-methoxy-1,4-benzoquinone, 2-hydroxy-1,4-naphthoquinone (lawsone), 2-hydroxy-3-methoxy-1,4-naphthoquinone, 2,5-dihydroxy-1,4-naphthoquinone, 2,5-dihydroxy-3-methyl-1,4-naphthoquinone, 5-hydroxy-1,4-naphthoquinone (juglone), 5,8-dihydroxy-1,4-naphthoquinone (naphthazarin), 2-methoxy-5-hydroxy-1,4-naphthoquinone, or 2,5,8-trihydroxy-1,4-naphthoquinone, in the form of an anhydrous solution or a powder.

13 Claims, No Drawings

COMPOSITION FOR COLORING SKIN

This invention relates to a composition for coloring or artificially colouring skin.

It is known to give skin an artificial coloration similar to that which it can acquire through exposure to sunlight.

Apart from exposure to UV radiation from UV lights, which activates natural pigmentation in skin, it is known that certain products, when applied to skin, develop a coloration due to a reaction between them and amino acids present in the epidermis. Examples of such products are α-hydroxy ketones, such as dihydroxyacetone, and α-hydroxyaldehydes, such a glyceraldehyde and erythrulose. The results obtained by use of these products are not satisfactory since development of the color on skin can be slow and tints obtained can be yellowish and consequently not particularly attractive.

French Pat. No. 2,065,465, German Pat. No. 2,051,947 and U.S. Pat. No. 3,781,418 describe a process for coloring skin using a composition comprising gamma-dialdehydes and meso-tartaraldehyde.

However, these compositions are not completely satisfactory, since they are not suitable for coloring all types of skin, and the brown coloration which is produced has very low resistance to washing with water.

U.S. Pat. Nos. 3,272,713 and 3,920,808 describe compositions intended to protect the skin against sunburn which can be applied to the skin in a one- or two-stage process. These compositions comprise a 1,4-benzoquinone or a 1,4-naphthoquinone and a compound containing a carbonyl group, which is dihydroxyacetone, 5-hydroxymethyl-2-furaldehyde, pyruvaldehyde, glyceraldehyde, alloxan or mono-hydroxyacetone.

Several applications of this composition are necessary to protect the skin effectively.

We have discovered that surprisingly when certain hydroxyquinones and meso-tartaraldehyde are together applied to the skin, a rapid coloration can appear, for example after about 10 minutes. This coloration shows good resistance to washing with water.

By a suitable choice of the hydroxyquinone or hydroxyquinones, the same natural brown coloration may be obtained on all types of skin.

The present invention therefore provides a two-component pack containing a composition for coloring or artificially tanning skin comprising two components (a) and (b) intended to be mixed at the time of use or to be applied to the skin successively wherein component (a) comprises meso-tartaraldehyde in the form of an aqueous solution, an aqueous gel or an aqueous emulsion, and component (b) comprises at least one hydroxyquinone, which is 2,5-dihydroxy-3-methyl-1,4-benzoquinone, 2,5-dihydroxy-3-methyl-6-methoxy-1,4-benzoquinone, 2-hydroxy-1,4-naphthoquinone (lawsone), 2-hydroxy-3-methoxy-1,4-naphthoquinone, 2,5-dihydroxy-1,4-naphthoquinone, 2,5-dihydroxy-3-methyl-1,4-naphthoquinone, 5-hydroxy-1,4-naphthoquinone (juglone), 5,8-dihydroxy-1,4-naphthoquinone (naphthazarin), 2-methoxy-5-hydroxy-1,4-naphthoquinone, or 2,5,8-trihydroxy-1,4-naphthoquinone, in the form of an anhydrous solution or a powder.

A composition comprising both components may be applied to the skin or each component may be applied separately. In this case component (b) is preferably applied before component (a).

Since hydroxyquinones are not particularly stable in the presence of water, when skin is to be colored in a single-stage process, component (a) is mixed with component (b) at the time of use.

Meso-tartaraldehyde is preferably present in the aqueous solution, gel or emulsion of component (a) in an amount of from 0.2 to 4%, more preferably from 0.5 to 2%, by weight relative to the total weight of components (a) and (b), whether they are applied simultaneously or successively.

The hydroxyquinone is preferably present in component (b), or in a composition comprising both components (a) and (b), in an amount of from 0.02 to 1% by weight, more preferably from 0.2 to 0.5% by weight, relative to the total weight of components (a) and (b), whether they are applied simultaneously or successively.

The present invention also provides a process for coloring or artificially tanning skin, generally to a natural brown color similar to that obtained by exposure of skin to solar rays, which comprises successively, in any order, applying to skin, a component (a) comprising meso-tartaraldehyde in the form of an aqueous solution, an aqueous gel or an aqueous emulsion, and a component (b) comprising at least one hydroxyquinone as defined above in the form of an anhydrous solution, or which comprises applying to skin a single composition comprising components (a) and (b) as defined above which may be prepared extemporaneously by mixing component (a) in the form of an aqueous solution, an aqueous gel or an aqueous emulsion and component (b) in the form of an anhydrous solution or in the from of a powder.

When component (b) is in the form of an anhydrous solution, the hydroxyquinone is preferably dissolved in an anhydrous solvent such as a saturated monohydric alcohol having 1 to 4 carbon atoms, preferably ethanol or isopropanol; a saturated long-chain monohydric alcohol having 10 to 18 carbon atoms; a polyol having 2 to 8 carbon atoms such as an alkylene glycol, for example ethylene glycol, propylene glycol, glycerol and diethylene glycol; a glycol ether such as a monoethylene glycol monoalkyl ether, a diethylene glycol monoalkyl ether and a triethylene glycol monoalkyl ether, for example ethylene glycol monoethyl ether, ethylene glycol monobutyl ether and diethylene glycol monoethyl ether; an acetic acid ester of ethylene glycol mono($C_{1-3}$)alkyl ether, such as ethylene glycol monomethyl ether acetate and ethylene glycol monoethyl ether acetate; and an ester of a saturated fatty acid, preferably having 14 to 16 carbon atoms, and a saturated alcohol having 1 to 4 carbon atoms, such as isopropyl myristate and isopropyl palmitate. As anhydrous solvents ethanol, cetyl alcohol, propylene glycol, ethylene glycol monoethyl ether and ethylene glycol monobutyl ether are preferred.

Both components (a) and (b) in the form of an anhydrous solution can contain at least one cosmetic adjuvant, such as a surfactant, preferably a nonionic surfactant; a thickener, in particular a cellulose derivative such as carboxymethylcellulose, hydroxypropylcellulose, hydroxymethylcellulose or hydroxyethylcellulose; a fatty alcohol; a fatty acid ester; a mineral, vegetable or animal oil; a perfume; a preservative; a UV-ray filtering agent or any other ingredient customarily used in cosmetic compositions for the skin.

When the two components (a) and (b) are mixed immediately before use, the mixture generally takes the form of a solution, gel or emulsion (cream or milk).

When the two components (a) and (b) are applied successively it is preferred to apply component (b) in the form of an anhydrous solution before component (a).

The pH of component (a) is generally from 3 to 8.5, and preferably from 4 to 6.5.

The pH of the composition comprising both components (a) and (b) is preferably from 3 to 7.

The invention is further illustrated by the following Examples.

EXAMPLE 1

The following artificial tanning composition is prepared:

| Component (a) | |
|---|---|
| Mixture of cetyl/stearyl alcohol and oxyethylenated cetyl/stearyl alcohol containing 15 moles of ethylene oxide, sold under the name SINNOWAX AO by HENKEL | 3 g |
| Glyceryl stearate | 1 g |
| Cetyl alcohol | 1 g |
| Isopropyl myristate | 3 g |
| Liquid paraffin | 6 g |
| Glycerin | 20 g |
| Meso-tartaraldehyde | 1.5 g |
| Perfumes, preservatives qs | |
| Water qs (quantity sufficient for) | 100 g |
| Comonent (b) | |
| 2,5-Dihydroxy-1,4-naphthoquinone | 0.2 g |
| Glycerin | 30 g |
| Hydroxypropylcellulose | 1 g |
| Ethyl alcohol qs | 100 g |

Component (a) is applied to the skin.

After 10 minutes, component (b) is applied.

The skin is colored in a tint similar to natural tanning, which persists after washing with water.

EXAMPLE 2

An artificial tanning composition is prepared extemporaneously by mixing component (a) containing 2 g meso-tartaraldehyde and perfumes and preservative in 100 g water and component (b) containing 0.06 g 2,5-dihydroxy-1,4-naphthoquinone, 0.10 g 2,5-dihydroxy-3-methyl-1,4-naphthoquinone, 1.6 g hydroxypropylcellulose and 15 g glycerin made up to 100 g with ethyl alcohol.

The resulting composition, containing the following per 100 g, is applied to skin:

| | |
|---|---|
| 2,5-Dihydroxy-1,4-naphthoquinone | 0.03 g |
| 2,5-Dihydroxy-3-methyl-1,4-naphthoquinone | 0.05 g |
| Hydroxypropylcellulose | 0.8 g |
| Glycerin | 7.5 g |
| Perfumes and preservatives qs (sufficient quantity) | |
| Ethyl alcohol | 41.60 g |
| Meso-tartaraldehyde | 1 g |
| Water qs | 100 g |

After 10 minutes the skin is colored in an increasingly dark brown tint similar to intensive tanning. This artificial tanning withstands the passage of time, even after washing.

EXAMPLE 3

The folowing artifical tanning composition is prepared:

| Component (a): | |
|---|---|
| Meso-tartaraldehyde | 0.75 g |
| Hydroxyethylcellulose | 1.0 g |
| Water qs | 100 g |
| Component (b): | |
| 2-Hydroxy-3-methoxy-1,4-naphthoquinone | 0.10 g |
| 2-Hydroxy-1,4-naphthoquinone | 0.10 g |
| Hydroxypropylcellulose | 2.0 g |
| Ethyl alcohol qs | 100 g |

Component (b) is applied to skin. After 10 minutes component (a) is applied.

The skin assumes a lightly tanned tint.

EXAMPLE 4

The following artificial tanning composition is prepared:

| Component (a): | |
|---|---|
| Meso-tartaraldehyde | 1.50 g |
| Propylene glycol | 20 g |
| 10% strength aqueous NaOH solution qs pH 5.5 | |
| Perfume, preservative qs | |
| Water qs | 100 g |
| Component (b): | |
| 2-Hydroxy-1,4-naphthoquinone | 0.15 g |
| Hydroxypropylcellulose | 0.70 g |
| Oleyl alcohol | 5 g |
| Propylene glycol | 20 g |
| Glycerin | 5 g |
| Ethyl alcohol qs | 100 g |

Component (b) is applied to skin. After 10 minutes component (a) is applied. The skin assumes a deeply tanned tint, possessing good persistence with the passage of time, even after washing with water.

EXAMPLE 5

A composition for coloring the skin is prepared extemporaneously, by mixing component (a) containing meso-tartaraldehyde in an emulsion containing cetyl alcohol, liquid paraffin, butyl glycol, glycerin, preservative, perfume, a mixture of cetyl/stearyl alcohol and oxyethylenated cetyl/stearyl alcohol containing 15 moles of ethylene oxide, sold under the name SINNOWAX AO by HENKEL, a mixture of non-self-emulsifying glycerol mono- and distearates and water and component (b) containing 3-methyl-2,5-dihydroxy-1,4-benzoquinone dissolved in ethyl alcohol.

The resulting composition, containing the following in 100 g, is applied to skin:

| | |
|---|---|
| Cetyl alcohol | 0.63 g |
| Meso-tartaraldehyde | 1.5 g |
| SINNOWAX AO | 1.9 g |
| Non-self-emulsifying mixture of glycerol mono- and distearates | 0.63 g |
| Liquid paraffin | 5.1 g |
| 2-Butoxyethanol | 1.27 g |
| Glycerin | 6.35 g |
| Preservative and perfume qs | |
| 3-Methyl-2,5-dihydroxy-1,1-benzoquinone | 0.02 q |
| Ethyl alcohol | 36.48 g |
| Water qs | 100 g |

After 10 minutes following the application, the skin becomes colored with an orange-brown tint which withstands the passage of time, even after washing.

EXAMPLE 6

A composition for coloring the skin is prepared extemporaneously by mixing component (a) containing meso-tartaraldehyde in the same emulsion as that of Example 5, and component (b) containing 3-methyl-6-methoxy-2,5-dihydroxy-1,4-benzoquinone dissolved in ethyl alcohol.

The resulting composition, containing the following in 100 g, is applied to skin:

| | |
|---|---|
| Cetyl alcohol | 0.63 g |
| Meso-tartaraldehyde | 1.5 g |
| SINNOWAX AO | 1.9 g |
| Non-self-emulsifying mixture of glycerol mono- and distearates | 0.63 g |
| Liquid paraffin | 5.1 g |
| 2-Butoxyethanol | 1.27 g |
| Glycerin | 6.35 g |
| Preservative and perfume qs | |
| 3-Methyl-6-methoxy-2,5-dihydroxy-1,4-benzoquinone | 0.04 g |
| Ethyl alcohol | 36.46 g |
| Water qs | 100 g |

After 10 minutes following application, the skin becomes colored with an orange-brown tint which withstands the passage of time, even after washing.

EXAMPLE 7

A composition for coloring the skin is prepared extemporaneously by mixing component (a) containing meso-tartaraldehyde in the same emulsion as that of Example 5, and component (b) containing 2-hydroxy-1,4-naphthoquinone dissolved in ethyl alcohol.

The resulting composition, containing the following in 100 g, is applied to skin:

| | |
|---|---|
| Cetyl alcohol | 0.63 g |
| Meso-tartaraldehyde | 1.5 g |
| SINNOWAX AO | 1.9 g |
| Non-self-emulsifying mixture of glycerol mono- and distearates | 0.63 g |
| Liquid paraffin | 5.1 g |
| 2-Butoxyethanol | 1.27 g |
| Glycerin | 6.35 g |
| Preservative and perfume qs | |
| 2-Hydroxy-1,4-naphthoquinone | 0.08 g |
| Ethyl alcohol | 36.42 g |
| Water qs | 100 g |

After 10 minutes following the application, the skin becomes colored with an orange-brown tint which withstands the passage of time, even after washing.

EXAMPLE 8

A composition for coloring the skin is prepared extemporaneously by mixing component (a) containing meso-tartaraldehyde in the same emulsion as that of Example 5, and component (b) containing 3-methyl-2,5-dihydroxy-1,4-benzoquinone, 2-hydroxy-1,4-naphthoquinone and 3-methyl-6-methoxy-2,5-dihydroxybenzoquinone dissolved in ethyl alcohol.

The resulting composition, containing the following in 100 g, is applied to skin:

| | |
|---|---|
| Cetyl alcohol | 0.63 g |
| Meso-tartaraldehyde | 1.5 g |
| SINNOWAX AO | 1.9 g |
| Non-self-emulsifying mixture of glycerol mono- and distearates | 0.63 g |
| Liquid paraffin | 5.1 g |
| 2-Butoxyethanol | 1.27 g |
| Glycerin | 6.35 g |
| Preservative, perfume qs | |
| 3-Methyl-2,5-dihydroxy-1,4-benzoquinone | 0.016 g |
| 2-Hydroxy-1,4-naphthoquinone | 0.073 g |
| 3-Methyl-6-methoxy-2,5-dihydroxybenzoquinone | 0.039 g |
| Ethyl alcohol | 36.4 g |
| Water qs | 100 g |

After 10 minutes following the application, the skin becomes colored with an intense red-brown tint, which is resistant even after washing.

EXAMPLE 9

The following composition for coloring the skin is prepared:

| | |
|---|---|
| Component (a): | |
| Meso-tartaraldehyde | 1.0 g |
| Hydroxyethylcellulose | 0.2 g |
| Ethyl alcohol | 10 g |
| NaOH qs pH 5 | |
| Water qs | 100 g |
| Component (b): | |
| 2-Methoxy-5-hydroxy-1,4-naphthoquinone | 0.05 g |
| Propylene glycol | 5 g |
| Ethyl alcohol qs | 100 g |

Component (b) is applied to skin. After 10 minutes component (a) is applied.

After about 20 minutes, the skin becomes colored with a yellow-brown tint which shows good persistance with the passage of time, even after washing with water.

EXAMPLE 10

The following composition for coloring the skin is prepared:

| | |
|---|---|
| Component (a) | |
| Meso-tartaraldehyde | 1 g |
| Hydroxyethylcellulose | 0.2 g |
| Ethyl alcohol | 10 g |
| NaOH qs pH 5 | |
| Water qs | 100 g |
| Component (b) | |
| 2,5,8-Trihydroxy-1,4-naphthoquinone | 0.04 g |
| 5-Hydroxy-1,4-naphthoquinone (juglone) | 0.2 g |
| Propylene glycol | 5 g |
| Ethyl alcohol qs | 100 g |

Components (b) and (a) are applied on the skin in the same manner as in Example 9. The skin becomes colored brown.

EXAMPLE 11

The following composition for coloring the skin is prepared:

| | |
|---|---|
| Component (a) | |
| Meso-tartaraldehyde | 1 g |
| Hydroxyethylcellulose | 0.2 g |
| Ethyl alcohol | 10 g |
| NaOH qs pH 5 | |
| Water qs | 100 g |

-continued

| Component (b) | |
|---|---|
| 5,8-Dihydroxy-1,4-naphthoquinone | 0.08 g |
| Propylene glycol | 5 g |
| Ethyl alcohol qs | 100 g |

Component (b) and (a) are applied in the same manner as in Example 9. The skin becomes colored red-brown.

EXAMPLE 12

A composition for coloring the skin is prepared extemporaneously by mixing component (a) containing:

| Meso-tartaraldehyde | 1 g |
|---|---|
| Water | 24 g |
| Ethyl alcohol qs | 100 g | and component (b) consisting of 0.05 g powdered 5-hydroxy-1,4-naphthoquinone (juglone).

After 20 minutes following the application, the skin becomes colored with a yellow-brown tint which withstands the passage of time, even after washing with soapy water.

We claim:

1. A two-component pack containing a composition for coloring or artificially tanning skin comprising two components (a) and (b) intended to be mixed at the time of use or to be applied to the skin successively wherein component (a) comprises meso-tartaraldehyde in the form of an aqueous solution, an aqueous gel or an aqueous emulsion, and component (b) comprises at least one hydroxyquinone, which is 2,5-dihydroxy-3-methyl-1,4-benzoquinone, 2,5-dihydroxy-3-methyl-6-methoxy-1,4-benzoquinone, 2-hydroxy-1,4-naphthoquinone, 2-hydroxy-3-methoxy-1,4-naphthoquinone, 2,5-dihydroxy-1,4-naphthoquinone, 2,5-dihydroxy-3-methyl-1,4-naphthoquinone, 5-hydroxy-1,4-naphthoquinone, 5,8-dihydroxy-1,4-naphthoquinone, 2-methoxy-5-hydroxy-1,4-naphthoquinone, or 2,5,8-trihydroxy-1,4-naphthoquinone, in the form of an anhydrous solution or a powder.

2. A pack according to claim 1 wherein component (b) is in the form of an anhydrous solution wherein the solvent is a saturated monohydric alcohol having from 1 to 4 carbon atoms, a saturated long-chain monohydric alcohol having from 10 to 18 carbon atoms, a polyol having from 2 to 8 carbon atoms, a glycol ether, an acetic acid ester of an ethylene glycol mono($C_{1-3}$)alkyl ether, or an ester of a $C_{4-16}$ saturated fatty acid and a saturated $C_{1-4}$-alcohol.

3. A pack according to claim 2 wherein the solvent is selected from the group consisting of ethanol, cetyl alcohol, propylene glycol, ethylene glycol monoethyl ether and ethylene glycol monobutyl ether.

4. A pack according to claim 1 wherein component (b) is in the form of a powder.

5. A pack according to claim 1, wherein component (a) comprises from 0.2 to 4% by weight of meso-tartaraldehyde and component (b) comprises from 0.02 to 1% by weight of the hydroxyquinone, both being relative to the total weight of components (a) and (b).

6. A pack according to claim 1, wherein the pH of component (a) comprising an aqueous solution or aqueous emulsion of meso-tartaraldehyde is from 3 to 8.5.

7. A pack according to claim 6 wherein the pH is from 4 to 6.5.

8. A pack according to claim 1, wherein the pH of the composition prepared by mixing all of components (a) and (b) together is from 3 to 7.

9. A pack according to claim 1, wherein component (a) or component (b) or both comprise at least one adjuvant which is a surfactant, thickener, fatty alcohol, fatty acid ester, mineral, vegetable or animal oil, perfume, preservative or UV-ray filtering agent.

10. A pack according to claim 1, wherein the form of the composition produced by mixing components (a) and (b) is a solution, emulsion or gel.

11. A two stage process for coloring or artificially tanning skin, which comprises applying to skin successively a component (a) and a component (b) or a component (b) and a component (a), component (a) comprising meso-tartaraldehyde in the form of an aqueous solution, an aqueous gel or an aqueous emulsion, and component (b) comprising a hydroxyquinone or hydroxyquinones selected fron the group consisting of 2,5-dihydroxy-3-methyl-1,4-benzoquinone, 2,5-dihydroxy-3-methyl-6-methoxy-1,4-benzoquinone, 2-hydroxy-1,4-naphthoquinone, 2-hydroxy-3-methoxy-1,4-naphthoquinone, 2,5-dihydroxy-1,4-naphthoquinone, 2,5-dihydroxy-3-methyl-1,4-naphthoquinone, 5-hydroxy-1,4-naphthoquinone, 5,8-dihydroxy-1,4-naphthoquinone, 2-methoxy-5-hydroxy-1,4-naphthoquinone, and 2,5,8-trihydroxy-1,4-naphthoquinone, in the form of an anhydrous solution.

12. A process for coloring or artificially tanning skin, which comprises applying to skin a composition obtained by mixing immediately before use a component (a) comprising meso-tartaraldehyde in the form of an aqueous solution, an aqueous gel or an aqueous emulsion and a component (b) comprising a hydroxyquinone or hydroxyquinones selected from the group consisting of 2,5-dihydroxy-3-methyl-1,4-benzoquinone, 2,5-dihydroxy-3-methyl-6-methoxy-1,4-benzoquinone, 2-hydroxy-1,4-naphthoquinone, 2-hydroxy-3-methoxy-1,4-naphthoquinone, 2,5-dihydroxy-1,4-naphthoquinone, 2,5-dihydroxy-3-methyl-1,4-naphthoquinone, 5-hydroxy-1,4-naphthoquinone, 5,8-dihydroxy-1,4-naphthoquinone, 2-methoxy-5-hydroxy-1,4-naphthoquinone, and 2,5,8-trihydroxy-1,4-naphthoquinone, in the form of an anhydrous solution or a power.

13. A process according to claim 11, wherein component (b) is applied before component (a).

* * * * *